United States Patent [19]

Sumner, Jr. et al.

[11] Patent Number: 5,169,994

[45] Date of Patent: Dec. 8, 1992

[54] PROCESS FOR THE MANUFACTURE OF 2,2,4,4-TETRAMETHYCYCLOBUTANEDIOL

[75] Inventors: Charles E. Sumner, Jr.; Bruce L. Gustafson; Jennifer R. Knight, all of Kingsport, Tenn.

[73] Assignee: Eastman Kodak Company, Rochester, N.Y.

[21] Appl. No.: 747,567

[22] Filed: Aug. 20, 1991

[51] Int. Cl.$^5$ ............................................. C07C 29/145
[52] U.S. Cl. ................................... 568/839; 568/301; 568/338
[58] Field of Search ...................... 568/338, 301, 839

[56] References Cited

U.S. PATENT DOCUMENTS

| | | | |
|---|---|---|---|
| 2,936,324 | 5/1960 | Hasek et al. | 260/617 |
| 3,000,906 | 9/1961 | Hasek et al. | 568/338 |
| 3,190,928 | 6/1965 | Elam et al. | 260/617 |

FOREIGN PATENT DOCUMENTS 965762  8/1964  United Kingdom ................ 568/300

OTHER PUBLICATIONS

Mugno et al., *Chim. Ind.* (Milan) 46(1), pp. 5-9 (1964); *Chemical Abstracts*, 60:9143f.

*Primary Examiner*—James H. Reamer
*Attorney, Agent, or Firm*—J. Frederick Thomsen; William P. Heath, Jr.

[57] ABSTRACT

Disclosed is a novel process for the manufacture of 2,2,4,4-tetramethylcyclobutanediol commencing with the pyrolysis of isobutyric anhydride to produce dimethylketene. Dimethylketene is absorbed into certain carboxylate ester solvents which function as the process solvents for subsequent dimerization of the dimethylketene to 2,2,4,4-tetramethylcyclobutanedione followed by the catalytic hydrogenation of the dione to the diol product.

6 Claims, No Drawings

PROCESS FOR THE MANUFACTURE OF 2,2,4,4-TETRAMETHYCYCLOBUTANEDIOL

This invention pertains to a novel, efficient process for the manufacture of 2,2,4,4 tetramethylcyclobutanediol starting with isobutyric anhydride. More particularly, this invention pertains to process wherein isobutyric anhydride is converted to dimethylketene which is absorbed by certain carboxylic ester solvents. The absorption solvent serves as the process solvent in subsequent dimerization and hydrogenation steps. Another embodiment of the invention pertains to the manufacture of dimethylketene by the pyrolysis of isobutyric anhydride at temperatures significantly lower than those employed in known processes.

2,2,4,4 Tetramethylcyclobutanediol is a valuable monomer which may be used in the preparation of a variety of polymeric materials which possess advantageous properties. For example, polyesters derived from dicarboxylic acids and 2,2,4,4 tetramethylcyclobutanediol possess higher glass transition temperatures and superior weatherability and hydrolytic stability when compared to like polyesters prepared from other commonly-used, polyester forming diols.

The preparation of dimethylketene by the pyrolysis of isobutyric anhydride is described in British Patent 965,762. Although the operating conditions such as the pyrolysis temperature, pressure and contact or residence time are broadly described, contact times of less than 1 second and temperatures and pressures of 500 to 600° C. and 100 torr to atmospheric are used in the examples. Mungo et al, Chim. Ind. (Milan), 46 (1), 5-9 (1964) (C.A. 60:9143f) teach the pyrolysis of isobutyric anhydride at an optimum temperature of 625° C. (measured on the wall of the pyrolysis reactor).

British Patent 965,762 also discloses the dimerization of dimethylketene to 2,2,4,4 tetramethylcyclobutanedione but provides essentially no details on the manner in which such dimerization may be carried out or the means by which the dione is recovered. The dimerization of undiluted dimethylketene presents heat transfer problems and thus is potentially hazardous. The Mungo et al reference acknowledges that dimethylketene is very dangerous because of its rapid peroxidation to explosive crystalline material.

U.S. Pat. Nos. 2,936,324 and 3,190,928 describe processes for the preparation of 2,2,4,4 tetramethylcyclobutanediol by the hydrogenation of the corresponding dione compound in the presence of nickel and ruthenium catalysts. These patents do not disclose any means by which the hydrogenation processes disclosed therein may be integrated with the dimethylketene manufacturing process.

The process provided by the present invention comprises the manufacture of 2,2,4,4 tetramethylcyclobutanediol from butyric anhydride wherein dimethylketene vapor is absorbed into a carboxylate ester which then functions as the process solvent for the conversion (dimerization) of dimethylketene to 2,2,4,4 tetramethylcyclobutanedione followed by hydrogenation of the dione to the diol. Thus, our novel process for the manufacture of 2,2,4,4 tetramethylcyclobutanediol comprises the steps of:

(1) feeding isobutyric anhydride to a pyrolysis zone wherein the isobutyric anhydride is heated at a temperature of about 350 to 600° C. to produce a vapor effluent comprising dimethylketene, isobutyric acid and unreacted isobutyric anhydride;

(2) rapidly cooling the vapor effluent to condense isobutyric acid and isobutyric anhydride and separating the condensate from the dimethylketene vapor;

(3) feeding the dimethylketene vapor to an absorption zone wherein the dimethylketene vapor is contacted with and dissolved in a solvent comprising an ester containing 4 to 20 carbon atoms and consisting of residues of an aliphatic carboxylic acid and an alkanol to produce an effluent comprising a solution of dimethylketene in the solvent;

(4) feeding the absorption zone effluent to a dimerization zone wherein the effluent is heated at 70 to 140° C. to convert dimethylketene to 2,2,4,4-tetramethylcyclobutanedione to produce an effluent comprising a solution of 2,2,4,4 tetramethylcyclobutanedione in the solvent; and (5) feeding the dimerization zone effluent to a hydrogenation zone wherein the effluent is contacted with a supported hydrogenation catalyst under hydrogenation conditions of pressure and temperature to produce an effluent comprising a solution of 2,2,4,4 tetramethylcyclobutanediol in the solvent.

The process provides a means for the non hazardous manufacture of 2,2,4,4 tetramethylcyclobutanediol at good rates and yields, e.g., in yields of 90% or greater based on the butyric anhydride consumed.

The first step of the process involves feeding isobutyric anhydride, usually in combination with an inert gas such as nitrogen, to the pyrolysis zone wherein the isobutyric anhydride is heated at about 350 to 600° C. under reduced pressure, e.g., 20 to 500 torr. Preferred conditions are temperatures in the range of 350 to 450° C., especially 400 to 435° C., and pressures of 40 to 250 torr. The contact or residence time of the reactant and product within the pyrolysis zone typically is in the range of about 1 to 8 seconds, depending on the temperatures and pressures employed. Step (1) preferably is carried out to achieve an average butyric anhydride conversion of at least 30%, preferably about 50 to 90%.

The second step of the process comprises rapidly cooling the pyrolysis effluent to condense the isobutyric acid by product of the pyrolysis reaction and unreacted butyric anhydride and separating the condensed liquids from the dimethylketene vapor to minimize the reaction of the isobutyric acid and dimethyl ketene. Cooling of the vapor stream may be accomplished using conventional equipment such as one or more heat exchangers or externally cooled cyclones which provide efficient heat removal. The cooling required by the second step normally should reduce the temperature of the pyrolysis effluent to at least 40° C., preferably about 20 to 30° C. The condensed isobutyric acid and isobutyric anhydride may be separated from the gaseous dimethylketene by conventional gas/liquid separation means such as one or more cyclones. When the pyrolysis step is carried out under reduced pressure, the temperature reduction and separation of the second step normally are performed at pressures substantially the same as those existing within the pyrolysis zone.

In the third step of our novel process, the dimethylketene vapor from the second step is contacted with and dissolved in an inert solvent having a boiling point (at standard temperature and pressure) of at least 75° C. and selected from esters containing 4 to 20 carbon atoms and consisting of the residue of an aliphatic, carboxylic acid and an alkanol. The carboxylate ester solvent preferably contains about 6 to 10 carbon atoms and has a boiling point (at standard temperature and pressure) of about 115 to 150° C. Examples of suitable solvents include isopropyl isobutyrate, isobutyl propionate, octyl acetate, isobutyl isobutyrate, isobutyl acetate and the like. Isobutyl isobutyrate constitutes the preferred solvent.

The absorption zone comprises apparatus which provides for intimate contact between the dimethylketene vapor and the liquid solvent. For example, the apparatus may consist of one or more columns equipped with packing material or trays wherein the dimethylketene vapor is fed at or near the bottom of the column and the solvent is fed at or near the top of the column resulting in the dissolution of the ascending gas by the descending liquid solvent. Alternatively, the solvent may be used as the liquid seal material in a liquid-sealed vacuum pump which provides the reduced pressure for the pyrolysis and cooling/separation zones. The dimethylketene gas is drawn through the pump wherein most of it is absorbed into the solvent. Any dimethylketene not absorbed in the vacuum pump may fed to and absorbed in a scrubber column as described above. Normally, the material absorbed in the solvent is a mixture of dimethylketene and 2,2,4,4 tetramethylcyclobutanedione, e.g., in dimethylketene:dione weight ratios of about 1:1 to 3:1. The concentration of dimethylketene and dione in the step (3) effluent may vary from about 12 to 20 weight percent, based on the total weight of the effluent.

The dimerization zone of the fourth step may comprise any apparatus which permits the step (3) effluent to be maintained at a temperature of about 70 to 140° C. for a period of time, e.g., a residence time of about 90 to 120 minutes, sufficient to convert the dimethylketene in the effluent to 2,2,4,4-tetramethylcyclobutanedione. Thus, the dimerization zone may consist of an agitated vessel equipped with a condenser and means to heat the step (3) effluent. The dimerization preferably is performed at a temperature of about 100 to 130° C. The product effluent of the dimerization zone comprises a solution of 2,2,4,4-tetramethylcyclobutanedione in the solvent, usually in a concentration of about 15 to 20 weight percent dione.

The final step of our process comprises the hydrogenation of the 2,2,4,4-tetramethylcyclobutanedione present in the step (4) effluent wherein the effluent is contacted with hydrogen at hydrogenation conditions of pressure and temperature in the presence of a hydrogenation catalyst, i.e., a catalyst which is effective to promote the hydrogenation of carbonyl compounds to their corresponding alcohols such as Raney nickel, Raney cobalt molybdenum promoted nickel, copper chromite and supported Group VIII metals. The hydrogenation preferably is carried out in the presence of a supported catalyst such as nickel on alumina, nickel on silica, ruthenium on carbon, platinum on alumina, platinum on carbon and palladium on carbon. The supported nickel catalyst are especially preferred. The hydrogenation conditions may be selected from temperatures and pressures in the range of about 100 to 2000 psig and 100 to 200° C. The conditions preferably are in the range of about 300 to 400 psig and 130 to 180° C.

The 2,2,4,4-tetramethylcyclobutanediol obtained from the hydrogenation step in accordance with the process described hereinabove may be isolated by means of conventional distillation and/or crystallization procedures. For example, the solvent may be removed as a vapor in a first distillation and then low boiling by-products such as 2,2,4-trimethyl-3-oxo-1-pentanol may be vaporized from the diol product in a second distillation. Finally, the product diol may be distilled, optionally under reduced pressure, to obtain substantially pure 2,2,4,4-tetramethylcyclobutanediol.

The present invention also provides a process for the manufacture of dimethylketene by contacting, for greater than 1 second, isobutyric anhydride at a temperature of about 350 to 450° C. and a pressure of less than 500 torr. In addition to lowering operating costs, the use of a lower temperature results in the formation of less decomposition products, thereby increasing the yield of dimethylketene based on the isobutyric anhydride converted. This embodiment of our invention preferably employs a contact time of about 4 to 8 seconds at 350 to 450° C. and a pressure of about 50 to 250 torr.

The processes provided by the present invention are further illustrated by the following examples. The apparatus used in the examples included a pyrolysis preheater consisting of a 3 foot section of 0.25 inch internal diameter, stainless steel tubing heated by an electric furnace. The preheater tubing was connected to the pyrolysis zone which consisted of a seven foot section of 0.25 inch internal diameter, stainless steel, tubing, also heated by an electric furnace. The pyrolysis tubing was connected to two 50 mL, glass cyclone separators arranged in series. Each cyclone separator had a 1 mm inlet port, was jacketed to permit cooling to 30° C. and was connected to an isobutyric recovery flask for receiving liquid isobutyric acid and isobutyric anhydride. Reduced pressure was maintained in the preheater, pyrolysis zone, cyclone separators and isobutyric recovery flask by means of a two stage, positive displacement, liquid seal, vacuum pump connected to the second of the cyclones and to the isobutyric recovery flask. Dimethylketene vapor was transported to the vacuum pump by the conduits connecting the cyclone and flask to the vacuum pump.

The vacuum pump was connected to the base of a 1 inch diameter by 24 inch tall, jacketed, absorption column filled with quartz chips and affixed to a 1000 mL absorption product flask. Isobutyl isobutyrate was fed to the reservoir of the vacuum pump and to the top of the packed column to absorb the dimethylketene vapor and the dimethylketene/isobutyl isobutyrate solutions were collected the absorption product flask. The dimethylketene/isobutyl isobutyrate solution was transferred to a dimerization zone consisting of a heated 1000 mL flask equipped with a mechanical stirrer and a condenser wherein the solution was heated to convert dimethylketene to 2,2,4,4-tetramethylcyclobutanedione.

The 2,2,4,4-tetramethylcyclobutanedione/isobutyl isobutyrate solution was transferred to the hydrogenation zone which consisted of a 1000 mL autoclave containing a basket of hydrogenation catalyst. The hydrogenation product was cooled, 2,2,4,4 tetramethylcyclobutanediol was collected by filtration and both the filter cake and filtrate were analyzed by gas chromatography.

EXAMPLE 1

A total of 228 g of isobutyric anhydride was pumped at a rate of 3.8 g (0.024 mole) per minute to the preheater tube heated at 300° C. and the pyrolysis tube heated at 425° C. which were maintained at approximately 250 torr. The vapor transported from the second cyclone to the vacuum pump consisted of 97+% dimethylketene. The amount of isobutyric anhydride consumed in the pyrolysis zone was 60% based on the amount of isobutyric fed and collected in the isobutyric recovery flask. Isobutyl butyrate was pumped through the reservoir of the vacuum pump at a rate of 5 mL per minute and to the top of the absorption column at a rate of 0.5 mL per minute. The combined absorption product solutions were heated at 120° C., first in the absorption product flask for 1 hour and then in the dimerization flask for 1 hour under an argon atmosphere. The dimerization product solution (370.3 g) containing 57.6 g of 2,2,4,4-tetramethylcyclobutanedione was hydrogenated at 145° C. under a hydrogen pressure of 350 psig for 6 hours in the presence of 20 g of a supported hydrogenation catalyst consisting of 58% nickel on kieselguhr. The catalyst was removed by hot filtration, the filtrate was cooled and the product was collected by filtration. The yield of 2,2,4,4-tetramethylcyclobutanediol was 55.5 g, 90% of theory based on the isobutyric anhydride converted in the pyrolysis zone.

EXAMPLE 2

The procedure described in Example 1 was repeated except that the hydrogenation was carried out at 145° C. using 20 g of a hydrogenation catalyst consisting of 31% nickel on amorphous silica alumina. The yield of 2,2,4,4-tetramethylcyclobutanediol was 60.4 g, 98% of theory based on the isobutyric anhydride converted in the pyrolysis zone.

EXAMPLE 3

The procedure described in Example 1 was repeated except that the combined absorption product solutions were heated at 90° C. for a total of 2 hours. The yield of 2,2,4,4-tetramethylcyclobutanediol was 41.9 g, 68% of theory based on the isobutyric anhydride converted in the pyrolysis zone.

The invention has been described in detail with particular reference to preferred embodiments thereof, but it will be understood that variations and modifications can be effected within the spirit and scope of the invention.

We claim:

1. Process for the manufacture of 2,2,4,4-tetramethylcyclobutanedione which comprises the steps of:
   (1) feeding isobutyric anhydride to a pyrolysis zone wherein the isobutyric anhydride is heated at a temperature of about 350 to 600° C. to produce a vapor effluent comprising dimethylketene, isobutyric acid and unreacted isobutyric anhydride;
   (2) rapidly cooling the vapor effluent to condense isobutyric acid and isobutyric anhydride and separating the condensate from the dimethylketene vapor;
   (3) feeding the dimethylketene vapor to an absorption zone wherein the dimethylketene vapor is contacted with and dissolved in a solvent comprising an ester containing 4 to 20 carbon atoms and consisting of residues of an aliphatic carboxylic acid and an alkanol to produce an effluent comprising a solution of dimethylketene in the solvent;
   (4) feeding the absorption zone effluent to a dimerization zone wherein the effluent is heated at 70 to 140° C. to convert dimethylketene to 2,2,4,4-tetramethylcyclobutanedione to produce an effluent comprising a solution of 2,2,4,4-tetramethylcyclobutanedione in the solvent; and
   (5) feeding the dimerization zone effluent to a hydrogenation zone wherein the effluent is contacted with a supported hydrogenation catalyst under hydrogenation conditions of pressure and temperature to produce an effluent comprising a solution of 2,2,4,4-tetramethylcyclobutanediol in the solvent.

2. Process of claim 1 wherein isobutyric anhydride is heated at a temperature of about 380 to 450° C. and a pressure of about 40 to 250 torr in the pyrolysis zone and the carboxylate ester solvent present in steps (3), (4) and (5) contains about 6 to 10 carbon atoms and has a boiling point of about 115 to 150° C.

3. Process of claim 2 wherein the absorption zone effluent is heated at a temperature of about 100 to 130° C. and the dimerization zone effluent is hydrogenated at about 100 to 200° C. and 100 to 2000 psig in the presence of a supported nickel catalyst.

4. Process for the manufacture of 2,2,4,4-tetramethylcyclobutanedione which comprises the steps of:
   (1) feeding isobutyric anhydride to a pyrolysis zone wherein the isobutyric anhydride is heated at a temperature of about 400 to 435° C. to produce a vapor effluent comprising dimethylketene, isobutyric acid and unreacted isobutyric anhydride;
   (2) rapidly cooling the vapor effluent to condense isobutyric acid and isobutyric anhydride and separating the condensate from the dimethylketene vapor;
   (3) feeding the dimethylketene vapor to an absorption zone wherein the dimethylketene vapor is contacted with and dissolved in isobutyl isobutyrate solvent to produce an effluent comprising a solution of dimethylketene in the solvent;
   (4) feeding the absorption zone effluent to a dimerization zone wherein the effluent is heated at 100 to 130° C. to convert dimethylketene to 2,2,4,4-tetramethylcyclobutanedione to produce an effluent comprising a solution of 2,2,4,4-tetramethylcyclobutanedione in the solvent; and
   (5) feeding the dimerization zone effluent to a hydrogenation zone wherein the effluent is contacted with a supported nickel hydrogenation catalyst at 130 to 180° C. and 300 to 400 psig to produce an effluent comprising a solution of 2,2,4,4-tetramethylcyclobutanediol in the solvent.

5. Process for the manufacture of dimethylketene which comprises the pyrolysis of isobutyric anhydride at a temperature of 350 to 450° C. and a pressure of less than 500 torr for greater than 1 second.

6. Process according to claim 5 wherein the isobutyric anhydride is heated at 350 to 450° C. at a pressure of about 50 to 250 torr for about 4 to 8 seconds.

* * * * *

UNITED STATES PATENT AND TRADEMARK OFFICE
CERTIFICATE OF CORRECTION

PATENT NO. : 5,169,994

DATED : December 8, 1992

INVENTOR(S) : Sumner, Jr. et al.

It is certified that error appears in the above-identified patent and that said Letters Patent is hereby corrected as shown below:

Column 5, line 47 (Claim 1, line 2) "cyclobutanedione" should be --- cyclobutanediol ---.

Column 6, line 27 (Claim 4, line 2) "cyclobutanedione" should be --- cyclobutanediol ---.

Signed and Sealed this

Twenty-second Day of March, 1994

Attest:

BRUCE LEHMAN

*Attesting Officer*  *Commissioner of Patents and Trademarks*